US00PP28924P3

(12) United States Plant Patent
Psenner

(10) Patent No.: US PP28,924 P3
(45) Date of Patent: Jan. 30, 2018

(54) ***BIDENS* PLANT NAMED 'BIDPOPSTA'**

(50) Latin Name: *Bidens ferulifolia*
Varietal Denomination: Bidpopsta

(71) Applicant: Thomas Psenner, Bozen (IT)

(72) Inventor: Thomas Psenner, Bozen (IT)

( * ) Notice: Subject to any disclaimer, the term of this patent is extended or adjusted under 35 U.S.C. 154(b) by 44 days.

(21) Appl. No.: 14/999,237

(22) Filed: Apr. 13, 2016

(65) Prior Publication Data

US 2016/0309639 P1 Oct. 20, 2016

(30) Foreign Application Priority Data

Apr. 14, 2015 (QZ) ..... PBR 2015/0836

(51) Int. Cl.
*A01H 5/02* (2006.01)

(52) U.S. Cl.
USPC ..... Plt./410

(58) Field of Classification Search
USPC ..... Plt./410
See application file for complete search history.

*Primary Examiner* — Susan McCormick Ewoldt

(57) ABSTRACT

A new cultivar of *Bidens* plant named 'Bidpopsta' that is characterized by a a compact habit, large yellow flowers and does not require the use of growth retardants to produce a plant having a compact habit.

1 Drawing Sheet

Botanical classification: *Bidens ferulifolia.*
Variety denomination: 'Bidpopsta'.

BACKGROUND OF THE INVENTION

The present invention relates to a new and distinct cultivar of *Bidens* plant botanically known as *Bidens ferulifolia* and hereinafter referred to by the cultivar name 'Bidpopsta'.

The new cultivar is the product of a breeding program conducted by the inventor in a cultivated area of Bozen, Italy. The objective of the breeding program is to develop new *Bidens* cultivars with large flowers and a compact habit.

'Bidpopsta' originated from the crossing in 2011 of the female or seed parent *Bidens* 'Bidrosta' (not patented) and the male or pollen parent *Bidens 'BID* 719' (U.S. Plant Pat. No. 22,271). The cultivar 'Bidpopsta' was selected by the inventor in 2013 as a single plant within the progeny of the stated cross in a controlled environment of Bozen, Italy.

Asexual reproduction by terminal cuttings of the new cultivar 'Bidpopsta' was first performed in 2013 in Bozen, Italy. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Bidens* cultivar 'Bidpopsta'. These traits in combination distinguish 'Bidpopsta' as a new and distinct cultivar apart from all other existing varieties of *Bidens* known to the inventor.

1. *Bidens* 'Bidpopsta' exhibits a compact habit.
2. *Bidens* 'Bidpopsta' exhibits large yellow flowers.
3. *Bidens* 'Bidpopsta' does not require the use of growth retardants to produce a plant having a compact habit.

*Bidens* 'Bidpopsta' can be compared to the *Bidens* cultivars 'Mega Charm' (not patented), and 'Bidy Gonzales' (not patented). In comparison to 'Mega Charm', 'Bidpopsta' has larger diameter flowers with wider petals than the flowers of 'Mega Charm'. 'Bidpopsta' has longer length leaves than the leaves of 'Mega Charm'. 'Bidpopsta' has a shorter length peduncle than the peduncle length of 'Mega Charm'. In comparison to 'Bidy Gonzales', 'Bidpopsta' has larger diameter flowers than the flowers of 'Bidy Gonzales'. 'Bidpopsta' has a less number of flowers than the number of flowers of 'Bidy Gonzales'. 'Bidpopsta' has longer length leaves than the leaves of 'Bidy Gonzales'.

The closest comparison variety is the male parent plant *Bidens* 'BID 719'. 'Bidpopsta' is different than 'BID 719' in having larger flowers that are almost double in diameter, a compact habit and does not does not require the use of growth retardants to produce a compact habit. In contrast, 'BID 719' has a spreading habit and requires the use of growth retardants.

The new cultivar 'Bidpopsta' is distinguishable from the female or seed parent plant 'Bidrosta' in having larger flowers. In contrast, the flowers of 'Bidrosta' are smaller.

BRIEF DESCRIPTION OF THE DRAWING

The accompanying photograph illustrates the distinguishing traits of *Bidens* 'Bidpopsta'. The plant in the photograph shows an overall view of a 16 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Bidens* cultivar named 'Bidpopsta'. Data was collected in Gensingen, Germany from 16 week old glass greenhouse grown plants in 12 cm. diameter containers. The time of year was Spring and the temperature averaged 20° Centigrade during the day and 17° Centigrade at night. The light level was 60 klux. No growth retardants were used. Color determinations are in accordance with The Royal Horticultural Society Colour Chart 2001 edition, except where general color terms of ordinary dictionary significance are used. The growing requirements are similar to the species.

'Bidpopsta' has not been tested under all possible conditions and phenotypic differences may be observed with variations in environmental, climatic, and cultural conditions, however, without any variance in genotype.

Botanical classification: *Bidens* 'Bidpopsta'.

Use: Ornamental.

Parentage: 'Bidpopsta' resulted from the crossing of the following parent plants:

*Female parent.*—*Bidens* 'Bidrosta'.

*Male parent.*—*Bidens* 'BID 719'.

Vigor: Moderate.

Growth habit: Broad spreading-upright.

Plant shape: Flattened globe shaped.

Suitable container size: 9 cm. and larger container.

Height: Average 14.2 cm. in height.

Width: Average 26.0 cm. in width.

Hardiness: USDA Zone 9.

Propagation: Terminal cuttings.

Time to initiate roots (summer): Approximately 10 days to produce roots on an initial cutting at 25° Centigrade.

Time to initiate roots (winter): Approximately 14 days to produce roots on an initial cutting at 16° Centigrade.

Time to produce a rooted cutting or liner (summer): Approximately 21 days at 21° Centigrade.

Time to produce a rooted cutting or liner (winter): Approximately 25 days at 18° Centigrade.

Crop time: From a rooted cutting, approximately 8 to 10 weeks are required to produce a finished flowering plant.

Root system: Fine and fibrous.

Stem:

*Branching habit.*—Free branching.

*Average number of lateral branches.*—8.

*Pinching.*—Yes.

*Lateral branch diameter.*—3 mm. in diameter.

*Lateral branch length.*—8.5 cm. in length.

*Lateral branch strength.*—High.

*Stem color.*—Upper surface 166A, bottom surface 145C.

*Pubescence.*—Covered with short soft hairs, 0.75 mm. in length, NN155A in color.

*Internode length.*—1.4 cm. between nodes.

*Shape.*—Round.

*Surface.*—Slightly glossy.

Foliage:

*Leaf arrangement.*—Opposite.

*Compound or single.*—Single.

*Quantity of leaves per lateral branch.*—14.

*Leaf length.*—3.9 cm. in length.

*Leaf width.*—4.2 cm. in width.

*Leaf shape.*—Roughly ovate overall, pinnatisect to bipinnatisect.

*Leaf apex.*—Acute.

*Leaf base.*—Cuneate.

*Leaf texture.*—Slightly glossy both surfaces.

*Pubescence.*—Both sides very sparsely covered with short soft hairs, 0.4 mm in length.

*Leaf margin.*—Deeply incised.

*Sinuses.*—Convergent.

*Leaf fragrance.*—Herb like when rubbed.

*Young leaf color* (*lower surface*).—144B.

*Young leaf color* (*upper surface*).—144A.

*Mature leaf color* (*lower surface*).—138B.

*Mature leaf color* (*upper surface*).—Varies between 137B and 141B.

*Vein color* (*lower surface*).—143A.

*Vein color* (*upper surface*).—144A.

*Leaf attachment.*—Petiolate.

*Petiole dimensions.*—9 mm. in length, 4 mm. in width and 2 mm. in height.

*Petiole color* (*upper surface*).—144B, margins 145C.

*Petiole color* (*lower surface*).—144A, margins 145C.

Inflorescence:

*Inflorescence type.*—Terminal and axillary capitulae.

*Inflorescence form.*—Solitary capitulae.

*Flowering habit.*—Continuous.

*Inflorescence aspect.*—Upward and outward.

*Quantity of inflorescences per lateral stem.*—1.

*Quantity of inflorescences and buds per plant.*—Average 220.

*Natural flowering season.*—Spring to late summer.

*Fragrance.*—Moderate, sweet.

*Rate of inflorescence opening.*—Terminal inflorescence opens first, followed by secondary and tertiary inflorescences.

*Flower dimensions.*—5.6 cm. in diameter and 1.4 cm. in height.

*Disc diameter.*—1.4 cm.

*Receptacle diameter.*—1.5 mm.

*Receptacle height.*—1.0 mm.

*Flower longevity.*—Approximately 14 days.

*Bud length.*—7.0 mm. in length.

*Bud diameter.*—8.0 mm. in diameter.

*Bud shape.*—Globe shaped.

*Bud color.*—7A, base 147B.

*Ray floret number.*—Average 10.

*Rows of ray florets.*—One.

*Ray floret aspect.*—Outward to slightly upward.

*Ray floret arrangement.*—Rotate.

*Ray floret shape.*—Ovate to oblong.

*Ray floret dimensions.*—3.0 cm. in length and 1.0 mm. in width.

*Ray floret fused or unfused.*—Unfused.

*Ray floret apex.*—Praemorse.

*Ray floret base.*—Attenuate.

*Ray floret texture.*—Smooth both surfaces.

*Ray floret color when opening* (*upper side*).—12A.

*Ray floret color when opening* (*under side*).—9A.

*Ray floret color fully open* (*upper side*).—14A.

*Ray floret color fully open* (*under side*).—14B.

*Ray floret color fading to.*—14A.

*Disc floret number.*—Average 120.

*Disc floret arrangement.*—Spiral on disc.

*Disc floret shape.*—Tubular.

*Disc floret apex.*—Acute.

*Disc floret base.*—fused.

*Disc floret texture.*—Smooth.

*Disc floret dimensions.*—8 mm. in length, 3 mm. in width at top, 0.75 mm. at base.

*Disc floret color* (*when opening*).—Base 157D, top 20A.

*Disc floret color* (*mature*).—Base and mid-section 150C, top 9A.

*Self-cleaning or persistent.*—Self-cleaning.

Phyllaries:

*Quantity.*—Average 30.

*Arrangement.*—Rotate in two whorls.

*Dimensions.*—7 mm. in length and 1.7 mm. in width.
*Shape.*—Narrow ovate.
*Apex.*—Acute.
*Base.*—Broad cuneate.
*Texture* (*upper surface*).—Smooth and glossy.
*Texture* (*lower surface*).—Dull and pubescent, hairs 1 mm. in length, NN155D in color.
*Color* (*upper surface*).—147D, 153C toward tip.
*Color* (*lower surface*).—148A, 153D toward tip.

Spines:
*Number of spines per disc floret.*—One.
*Shape.*—Linear.
*Apex.*—Acute.
*Base.*—Broad cuneate.
*Texture.*—Smooth and glossy.
*Color.*—Base 150D, mid-section 151D, tip 171B.

Peduncle:
*Peduncle dimensions.*—3.5 cm. in length and 2.5 mm. in diameter.
*Peduncle angle.*—0°.
*Peduncle color.*—148A.
*Peduncle texture.*—Matte and smooth, covered with very short soft hairs.
*Peduncle strength.*—Strong.

Reproduction organs:
*Stamen number.*—5 in number.
*Anther shape.*—Basifixed, linear.
*Anther dimensions.*—2 mm. in length.
*Anther color.*—203B.
*Amount of pollen.*—Low.
*Pollen color.*—17A.
*Pistil number.*—One, on both ray and disc florets.
*Pistil length.*—6 mm.
*Stigma shape.*—Decurrent.
*Stigma color.*—13B.
*Style length.*—5 mm.
*Style color.*—150D.
*Ovary color.*—145C.

Fruit and seed: Fruit and seed production has not been observed to date.

Disease resistance: Plants of the new *Bidens* have not been observed for disease resistance.

The invention claimed is:

1. A new and distinct variety of *Bidens plant* named 'Bidpopsta' as described and illustrated.

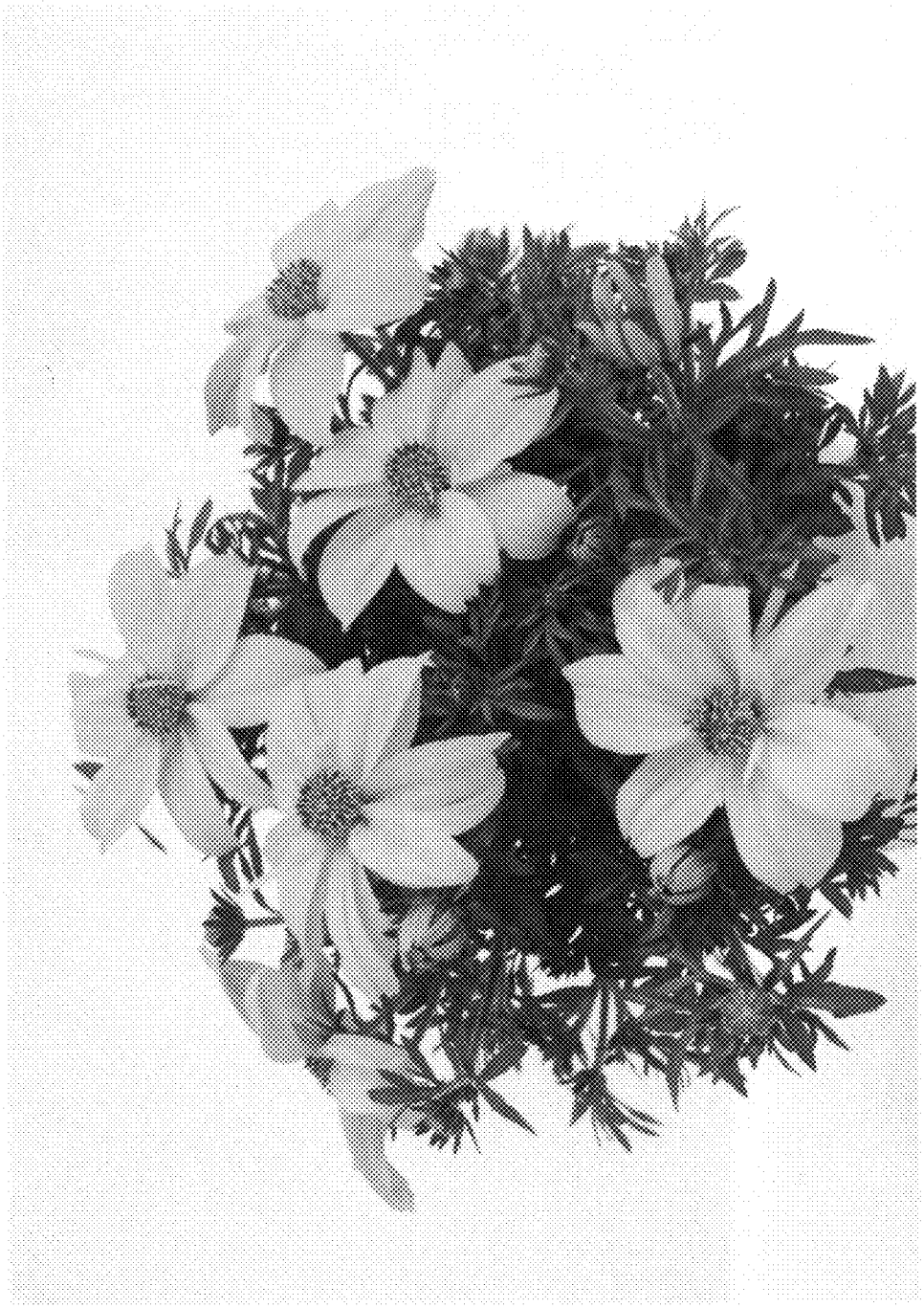

* * * * *